United States Patent [19]

Levy et al.

[11] Patent Number: 5,346,489
[45] Date of Patent: Sep. 13, 1994

[54] MEDICAL LASER DELIVERY SYSTEM

[75] Inventors: Michael B. Levy, Woodinville; Steven E. Wojcik, Bothell, both of Wash.

[73] Assignee: Luxar Corporation, Bothell, Wash.

[21] Appl. No.: 977,665

[22] Filed: Nov. 18, 1992

[51] Int. Cl.[5] .............................................. A61B 17/36
[52] U.S. Cl. ...................................... 606/15; 606/16; 606/19
[58] Field of Search .............................. 606/13, 16–19; 128/395–398; 433/29, 215, 216; 607/88, 89

[56] References Cited

U.S. PATENT DOCUMENTS

| | | | |
|---|---|---|---|
| 3,913,582 | 10/1975 | Sharon | 606/19 |
| 4,144,888 | 3/1979 | Malyshev et al. | 606/19 |
| 4,403,957 | 9/1983 | Mössle et al. | 433/29 |
| 4,421,382 | 12/1983 | Doi et al. | 606/16 |
| 4,521,194 | 6/1985 | Myers et al. | 433/215 |
| 4,538,609 | 9/1985 | Takenaka et al. | 606/16 |
| 4,608,980 | 9/1986 | Aihara | 606/16 |
| 4,818,230 | 4/1989 | Myers et al. | 433/215 |
| 4,826,431 | 5/1989 | Fujimura et al. | 433/215 |
| 4,849,859 | 7/1989 | Nagasawa | 606/16 |
| 4,911,712 | 3/1990 | Harrington | 606/14 |
| 4,917,083 | 4/1990 | Harrington et al. | 606/15 |
| 4,940,411 | 7/1990 | Vassiliadis et al. | 433/215 |
| 5,005,944 | 4/1991 | Laakmann et al. | 350/96.32 |
| 5,055,048 | 10/1991 | Vassiliadis et al. | 433/215 |

*Primary Examiner*—Stephen C. Pellegrino
*Assistant Examiner*—M. Peffley
*Attorney, Agent, or Firm*—Seed and Berry

[57] ABSTRACT

A medical laser delivery system usable to transmit laser energy from a laser energy source to a surgical site of a patient. The delivery system includes a handpiece adapted for rotatable coupling to a delivery arm coupled to the laser energy source such that the handpiece is rotatable about its longitudinal axis with respect to the delivery arm. A distal delivery system is coupled to the handpiece and delivers laser energy to the surgical site when the laser energy source is actuated. The handpiece includes a handpiece body adapted for rotatable coupling to the delivery arm and a handpiece head coupled to both the handpiece body and the distal delivery system. The handpiece head can be rotatably coupled to the handpiece body. In one embodiment, the handpiece head is angularly oriented at a fixed angle with respect to the handpiece body. In an alternative embodiment, the handpiece head is pivotally coupled to the body such that the handpiece head may be adjusted to various angles with respect to the handpiece body, such pivotal coupling preferably being accomplished by a ball and socket joint. A removable fiber extension is positioned within the handpiece and transmits laser energy from a fiber in the delivery arm to the distal delivery system. The distal delivery system includes an interchangeable delivery tip through which the laser energy is delivered to the surgical site. The tip can be a solid or hollow fiber of various sizes and shapes.

42 Claims, 6 Drawing Sheets

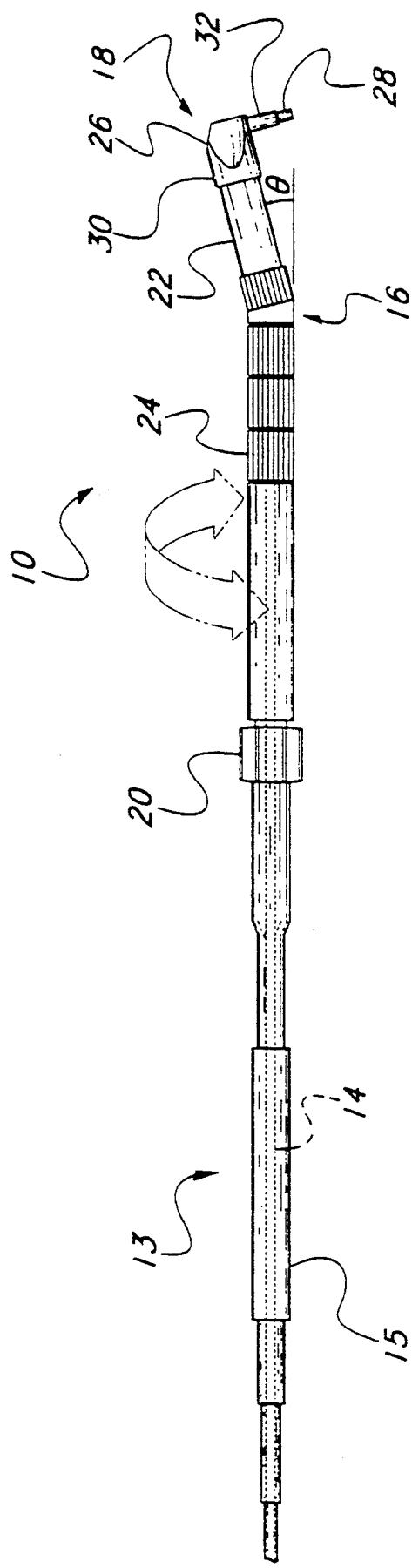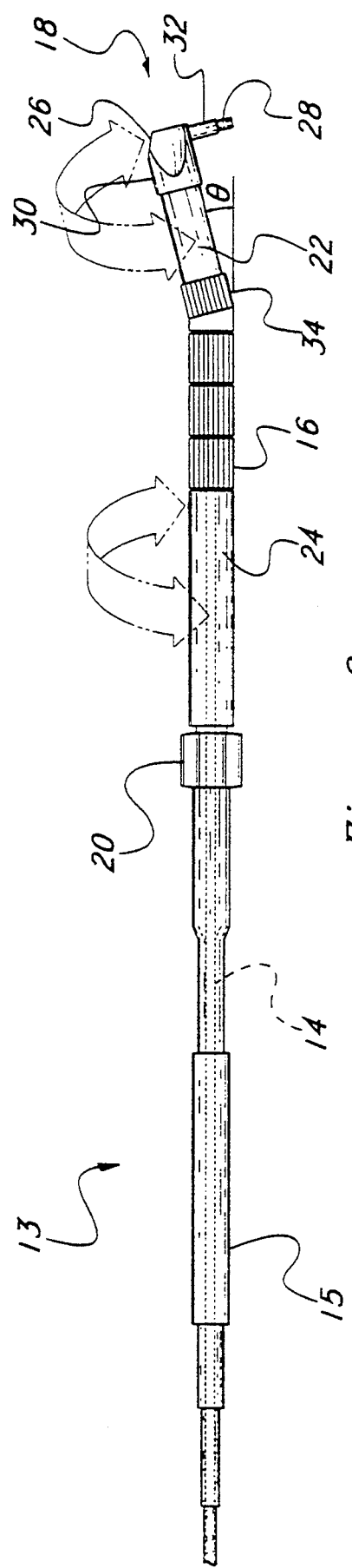
Figure 2
Figure 3

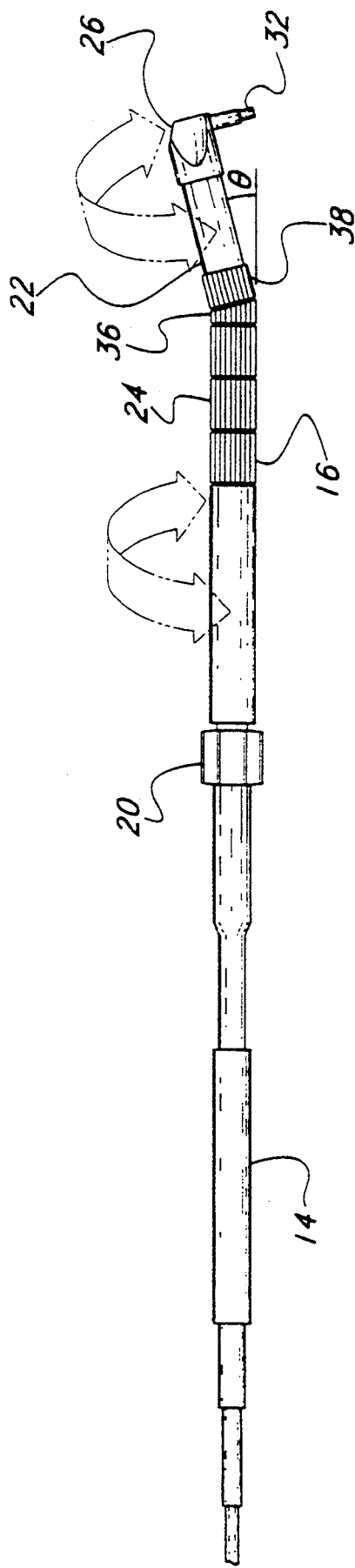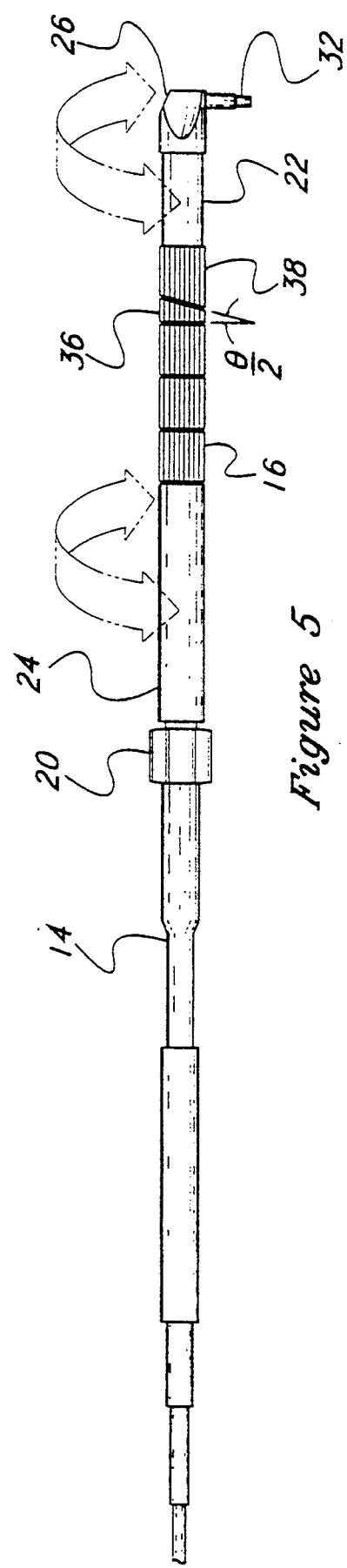

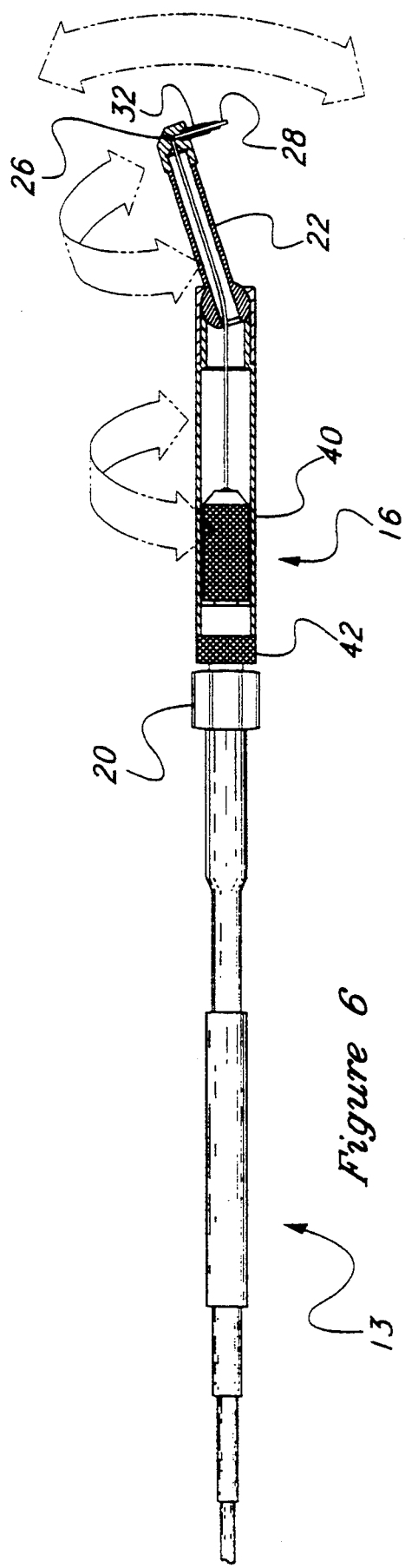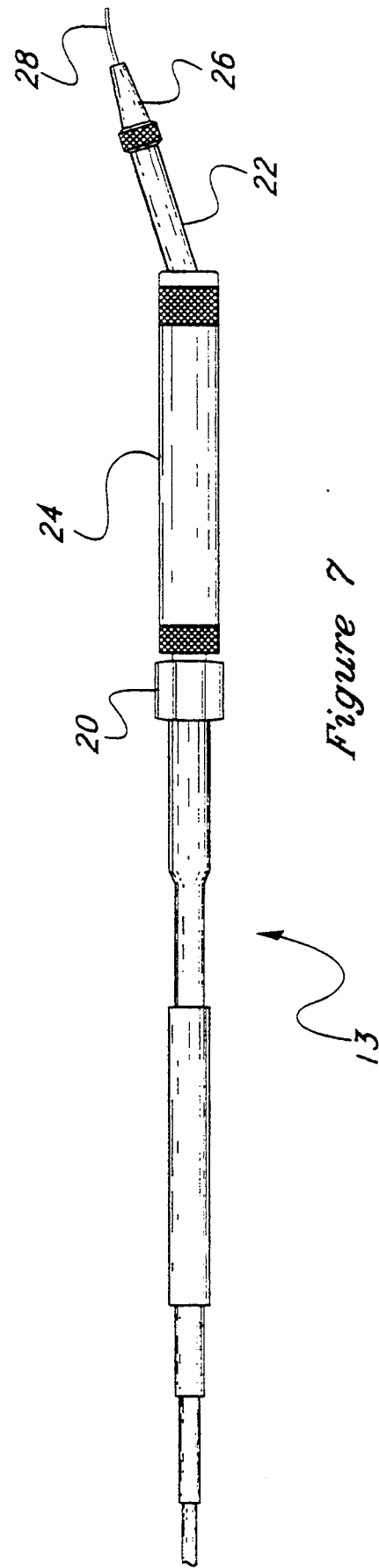

MEDICAL LASER DELIVERY SYSTEM

TECHNICAL FIELD

This invention relates to medical laser systems, and more particularly, to medical laser delivery systems that are highly adjustable to provide improved accessibility to surgical sites.

BACKGROUND OF THE INVENTION

Lasers are widely used for many medical applications, both internal and external of a patient. The laser offers many advantages over conventional modalities, among which are its precision, its ability to achieve hemostasis, and its ability to sterilize the surgical site. One of its greatest potential advantages is its ability to access non-line of sight areas or areas of the body that are otherwise difficult to reach. However, current laser systems suffer from awkwardness, the inability to access many areas of the body, particularly in comparison to currently used older surgical instruments, and the inability to adequately ensure sterility of the parts of the laser that come in contact with the patient.

Neodymium doped Yttrium Aluminum Garnet (Nd:YAG) lasers, such as offered by American Dental Laser, are sometimes offered with bent handpieces which curve the distal end of the fiber at an angle of about 30 degrees over the last centimeter, but these systems are still cumbersome since the angled portion cannot readily rotate with respect to the axis of the fiber and the geometrical configuration is not optimum for oral cavity access. Handheld carbon dioxide ($CO_2$) lasers, such as those manufactured by Directed Energy Systems or ILT, have a "delivery system" in which the distal end is too large and cumbersome to adequately reach into many parts of the body such as the oral cavity. The delivery system, such as it exists, consists of a focusing lens and a barrel of relatively large outer diameter. Articulating arm systems for $CO_2$ lasers are not outfitted with small tips, which makes access to the back molars of the mouth, for example, very difficult.

An additional accessibility problem with both types of lasers as well as non-laser surgical instruments is the inability to vary the angle of the distal portion of the instrument with respect to the proximal portion. When using these prior art laser and non-laser instruments, it is necessary to completely switch instruments in order to achieve a proper angle. In addition to wasting valuable surgical time by switching instruments, the expense of surgery is greatly increased because of the requirement for duplicative instruments.

SUMMARY OF THE INVENTION

The present invention overcomes the disadvantage of prior art instruments by providing a highly adjustable medical laser delivery system. The medical laser delivery system of the present invention is usable in conjunction with a laser energy source and a delivery arm coupled to the laser energy source. A preferred embodiment of the invention includes a handpiece rotatably coupled to the delivery arm such that the handpiece is rotatable about its longitudinal axis. The delivery arm includes a flexible fiber positioned within a casing, the fiber transmitting the laser energy from the laser energy source to the handpiece. The fiber may be solid or hollow. A distal delivery system is coupled to the handpiece, the distal delivery system delivers laser energy to a surgical site when the laser energy source is actuated.

In a preferred embodiment the handpiece includes a handpiece body rotatably coupled to the delivery arm and a handpiece head coupled to the handpiece body and to the distal delivery system. Preferably, the handpiece head is rotatably coupled to the handpiece body. In one embodiment, the handpiece head is angularly coupled to the handpiece body such that the head forms a fixed angle with respect to the body. In an alternate embodiment, the handpiece head is pivotally coupled to the body such that the head forms a variable angle with respect to the body. Preferably, the pivotal coupling is accomplished by a ball and socket joint.

The delivery arm fiber extends through the handpiece body to deliver the laser energy to the distal delivery system. In cases where the fiber may be damaged by repeated flexure, a removable, replaceable fiber extension may be positioned within the handpiece. The fiber extension communicates with the delivery arm fiber to receive the laser energy transmitted by the fiber from the laser energy source. The fiber extension transmits the laser energy to the distal delivery system when the laser energy source is actuated. A collet chuck is positioned within the handpiece, wherein the fiber extension removably mates with the collet chuck.

In a preferred embodiment, the distal delivery system includes a removable tip through which the laser energy is delivered to the surgical site. The tip may be a solid fiber or a hollow fiber. The distal delivery system includes a nozzle coupled between the handpiece and the tip. The nozzle includes a proximal end portion coupled to the handpiece and a distal end portion coupled to the tip. The distal portion can be angled with respect to the proximal end portion at an angle other than 180°. The nozzle may include a turning mirror positioned interiorly of the nozzle to reflect the laser energy from the proximal end portion to the distal end portion.

BRIEF DESCRIPTION OF THE DRAWINGS

FIG. 2 is an enlarged side elevational view of a rotatable handpiece and a distal delivery system of the medical laser system of FIG. 1.

FIG. 3 is a side elevational view of a first alternative embodiment of the rotatable handpiece and distal delivery system of FIG. 2.

FIG. 4 is a side elevational view of a second alternative embodiment of the rotatable handpiece and distal delivery system of FIG. 2.

FIG. 5 is a side elevational view of the rotatable handpiece and distal delivery system of FIG. 4 shown with a straight configuration.

FIG. 6 is a side elevational, cross-sectional view of a third alternative embodiment of the rotatable handpiece and distal delivery system of FIG. 2 using a ball and socket joint.

FIG. 7 is a side elevational view of the rotatable handpiece and distal delivery system of FIG. 6 shown with a straight nozzle configuration.

DETAILED DESCRIPTION OF THE INVENTION

Figure 1:
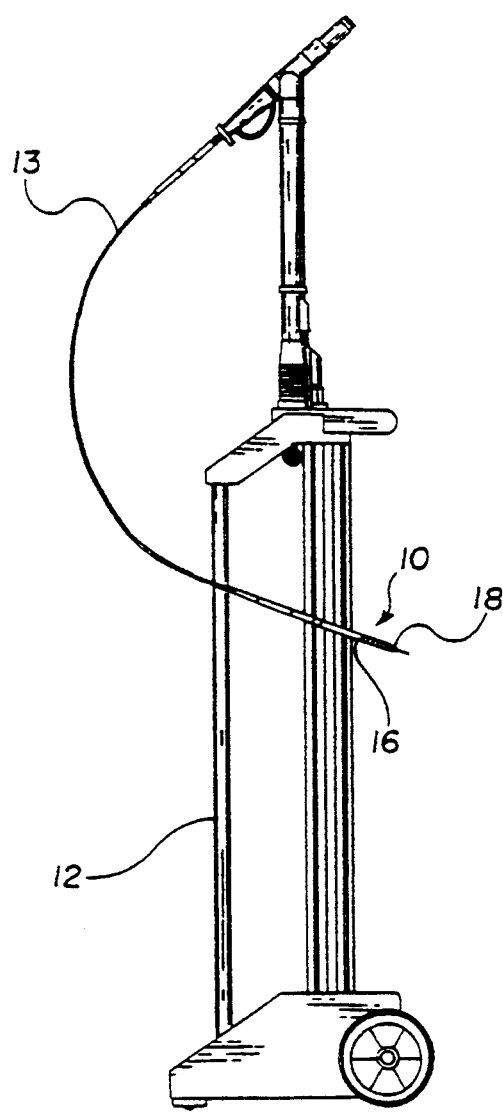
FIG. 1 is a side elevational view of a medical laser delivery system according to the present invention.

As shown in the drawings for purposes of illustration, the present invention is embodied in a medical laser delivery system 10 that delivers laser energy to a surgical site of a patient. The inventive delivery system 10 is most advantageously used in dental surgery, although many other medical uses are envisioned. The delivery system 10 receives laser energy from a laser energy source 12 through an elongated delivery arm 13 as shown in FIG. 1. The delivery arm preferably includes a flexible, solid or hollow fiber 14 positioned within a flexible casing 15, the fiber transmitting the laser energy from the source to a handpiece 16. The fiber may extend through the handpiece to a distal delivery system 18 coupled to the handpiece. The distal delivery system delivers the laser energy received from the handpiece to the surgical site.

Shown in FIG. 2 is an enlarged view of the handpiece 16, the distal delivery system 18, and a portion of the delivery arm 13. The delivery arm 13 is of conventional design, which is commonly either an articulated arm assembly or a flexible cable, both of which are shown in co-pending application Ser. No. 07/897,252 assigned to Luxar Corporation, which is incorporated herein by reference. In the articulated arm design, a series of mirrors within the arm transmit the laser energy from the laser energy source 12 to the handpiece 16. The flexible cable can include a fiber 14 within a casing 15 or can include a single member (not shown) that acts as both a fiber and casing.

The handpiece 16 is connected to the delivery arm 13 by a swivel joint 20. The swivel joint 20 allows the handpiece to rotate about its longitudinal axis while the delivery arm remains stationary as discussed in more detail in conjunction with FIG. 8. Preferably, the handpiece 16 includes a handpiece head 22 formed integral with or coupled to an elongated handpiece body 24. The handpiece body is rotatably coupled to the delivery arm 13 by the swivel joint 20. In the embodiment shown in FIG. 2, the handpiece head 22 is positioned at a fixed angle $\theta$ with respect to the longitudinal axis of the handpiece body 24.

The distal delivery system 18 is attached to the handpiece head 22. The distal delivery system includes a nozzle 26 and a removable and replaceable fiber delivery tip 28. The nozzle 26 has a proximal end portion 30 coaxially coupled to the handpiece head 22 and a distal end portion 32 positioned at a fixed angle of about 90° with respect to the proximal end portion. The distal end portion 32 holds the delivery, tip 28. Alternatively, the nozzle 26 may be straight with the distal portion aligned coaxial with the proximal portion and the longitudinal axis of the handpiece head 22, as shown in the embodiment of FIG. 7. The delivery tip 28 is attached to the distal end portion 32 of the nozzle 26 and delivers the laser energy to the surgical site. The delivery tip may be a hollow or a solid optical fiber or a so-called "contact tip" which has a metal, quartz or sapphire end that is heated by the laser energy and cuts by contacting the surgical site.

An alternate embodiment similar to the embodiment of FIG. 2 is shown in FIG. 3. This embodiment includes a swivel joint 34 at the intersection between the handpiece head 22 and the handpiece body 24. The swivel joint allows the handpiece head to rotate about its longitudinal axis and relative to the handpiece body. This added degree of movement adds flexibility that is absent from both prior art laser and non-laser dental instruments.

Another alternate embodiment is shown in FIGS. 4 and 5. The embodiment also allows the handpiece head 22 to rotate relative to the handpiece body 24 in addition to the handpiece body rotating with respect to the delivery arm 13. The handpiece body 24 of the embodiment of FIGS. 4 and 5 includes a body shank 36 rotatably coupled to a head shank 38 of the handpiece head 22, instead of the swivel joint 34 of FIG. 3. The body shank 36 is attached to the handpiece body 24 and the head shank 38 is attached to the handpiece head 22. Adjacent sides of the two shanks are each cut at an angle of $\theta/2$ to produce a maximum angle $\theta$ between the handpiece head 32 and the handpiece body 24 as shown in FIG. 4. When the handpiece head is rotated with respect to the handpiece body to the position shown in FIG. 5, the angles of the two shanks oppose each other and cancel each other out to produce a straight handpiece.

Figure 8:
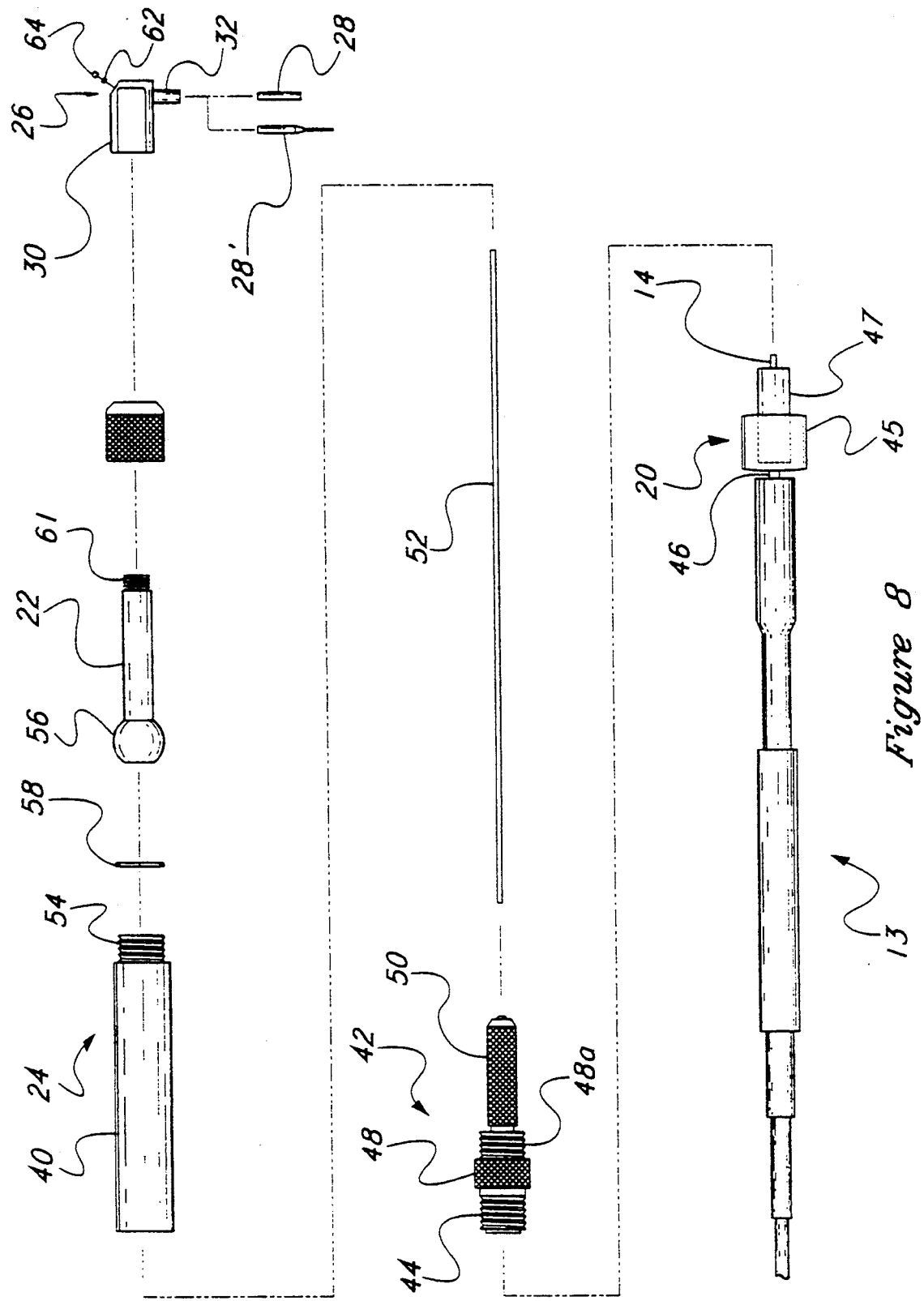
FIG. 8 is an exploded view of the handpiece and distal delivery system of FIG. 6.

Shown in FIGS. 6 through 8 is yet another alternate embodiment which provides even more versatility. In this embodiment, the handpiece body 24 has a body barrel 40 having a coaxial handpiece adapter 42 positioned partially within the body barrel. The adapter has a threaded shoulder member 44 that is threadably attached to a threaded collar 45 rotatably mounted on the delivery arm 13. The collar 45 is rotatably mounted on a coaxial neck 46 that is fixedly attached to the casing 15 of the delivery arm 13. A tubular insert 47 is coaxially attached to the neck 46 so that the collar 45 rotates with respect to the neck and insert. The shoulder member 44 is positioned on the insert 47 when threadably attached to the collar 45 to that the shoulder rotates with the collar with respect to the neck and insert. The collar 45, the shoulder member 44, neck 46, and insert 47 together comprise the preferred swivel joint 20 used in the embodiment of FIGS. 2-8 that allows the handpiece 16 to rotate with respect to the delivery arm 13.

Figure 9:
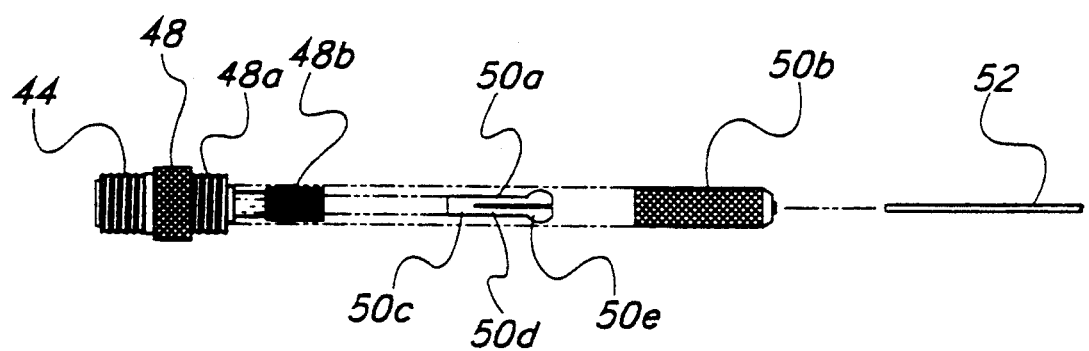
FIG. 9 is an exploded view of a handpiece adapter as used in the embodiments shown in FIGS. 6–8.

The adapter 42 also includes an intermediate member 48 with a first threaded insert portion 48a which projects into and is fixedly coupled to the body barrel 40. The adapter 42 further includes a collet chuck 50 positioned at an end of the adapter opposite the shoulder member 44 and fully within the body barrel 40. The intermediate member 48 has a second insert portion 48b which projects from the first insert portion 48a to within a central aperture of the collet chuck 50 to removably support the collet chuck as shown in FIG. 9. The collet chuck 50 includes a collet 50a that is coaxially positioned within a clamp nut 50b. The collet 50a includes an insert portion 50c that is inserted in the adapter second insert portion 48b. The collet 50a is slotted to form a plurality of fingers 50d, each with radially protruding shoulders 50e. The clamp nut 50b is placed onto the collet 50a and screwed onto the adapter second insert portion 48b. A flexible extension fiber 52 is inserted into the collet 50a and the adapter second insert portion 48b to abut the fiber 14 and receive the laser energy transmitted from the laser energy source 12 and transmit the laser energy to the nozzle 26. When the clamp nut 50b is screwed sufficiently on the adapter second insert portion, the collet fingers 50d are clamped down on the extension fiber 52 to removably retain the extension fiber. This allows the extension fiber 52 to be firmly connected to both the collet chuck 50 and the nozzle 26 while allowing the handpiece to rotate with respect to the delivery arm 13 without damaging the extension fiber. The extension fiber 52 is replaceable if it wears out.

The body barrel 40 of the handpiece body 24 also has an externally threaded socket 54 sized to matingly receive a ball swivel 56 fixedly attached to one end of the handpiece head 22 as shown in FIG. 8. An O-ring 58 is positioned between the ball swivel 56 and socket 54. A socket clamp nut 60 is positioned around the ball swivel and O-ring and is threadably received on the threaded exterior of the socket 54. The O-ring allows the socket clamp nut 60 to be threaded loosely enough to allow a user to angularly adjust the handpiece head 22 relative to the handpiece body 24 yet tightly enough to hold the two with a selected angular orientation. This arrangement provides a secure fitting between the handpiece head 22 and handpiece body 24 while still allowing their selective angular adjustment and free rotation of the handpiece head about its longitudinal axis relative to the delivery arm 13. With this arrangement, the angle between the handpiece head and the handpiece body may be set to any angle within the adjustment range provided. The extension fiber 52 extends through the handpiece head 22 and bends as required during angular adjustment of the handpiece hand relative to the handpiece body 24.

The handpiece head 22 includes an externally threaded end portion 61 opposite the ball swivel 56. The end portion 61 screws into the proximal portion 30 of the nozzle 26 for secure connection. This connection couples the nozzle 26 to the handpiece head 22 such that the nozzle moves with the handpiece head.

Instead of using a fiber extension 52, the delivery arm fiber 14 can simply be made long enough to extend to the nozzle 26. In such an embodiment, the adapter 42 is unnecessary. To complete the swivel joint 20, the handpiece body 24 is equipped with a threaded shoulder member similar to the adapter shoulder member 44. Such a handpiece body shoulder member is coupled to the delivery arm collar 45 in the same way as described above using the adapter shoulder member 44.

With any of the described embodiments of the invention, the delivery system 10 is preferably fitted with an interchangeable nozzle 26 for more versatility. As discussed above, the nozzle can be straight or angled.

When using the right-angled nozzle 26 shown in FIGS. 1-6 and 8, means must be provided to angularly direct the laser energy from the proximal end portion 30 of the nozzle 26 to its distal end portion 32. This preferably is accomplished using a turning mirror 62 positioned within the nozzle 26, as best shown in FIG. 8. The laser energy exits a distal end portion of the extension fiber 52, which extends into the proximal end portion 30 of the nozzle, and is directed toward the turning mirror 62. The turning mirror reflects the energy to the delivery tip 28, which extends into the distal end portion 32 of the nozzle. A set screw 64 is used to fix the position of the turning mirror 62 to provide proper transmission of the laser energy from the proximal end portion to the distal end portion of the nozzle.

A further means of providing adaptability is provided by using interchangeable fiber delivery tips 28 of various sizes and shapes. The delivery tip can be straight, as shown in FIG. 6, or can be curved, as shown in FIG. 7. FIG. 8 shows two alternate interchangeable delivery tips 28 and 28'. The delivery tip 28' is an endodontic tip being longer than and having a smaller diameter than the straight delivery tip 28. By using different sized and shaped nozzles 26, the user can adapt the delivery tip 28 according to the accessibility of the surgery site.

The variability of the diameters of the interchangeable delivery tips 28 provides an additional benefit that is not possible with conventional single-sized tips. The variable diameter of the tips provides a laser energy beam size that is variable. This allows the user to take advantage of an additional benefit of using a laser, which is the ability of the laser to achieve hemostasis or blood clotting. A user can employ a small diameter delivery tip to produce a narrow beam for cutting, and then easily switch to a larger diameter delivery tip to produce a comparatively wide beam to achieve hemostasis.

From the foregoing it will be appreciated that, although specific embodiments of the invention have been described herein for purposes of illustration, various modifications may be made without deviating from the spirit and scope of the invention. Accordingly, the invention is not limited except as by the appended claims.

We claim:

1. A medical laser delivery system usable in conjunction with a laser energy source and a delivery arm coupled to the laser energy source to transmit laser energy, comprising:

a handpiece adapted for rotatable coupling to the delivery arm, the handpiece including transmission means for transmitting the laser energy received from the delivery arm, the handpiece being rotatable about its longitudinal axis;

means for preventing the handpiece from decoupling from the delivery arm when rotating the handpiece during use: and a distal delivery .system coupled to the handpiece, the distal delivery system delivering the laser energy received from the handpiece to a surgical site when the laser energy source is actuated;

wherein the handpiece includes a handpiece body adapted for rotatable coupling to the delivery arm and a handpiece head having one end coupled to the handpiece body and another end coupled to the distal delivery system;

wherein the handpiece head is rotatably coupled to the handpiece body, the handpiece head being rotatable about its longitudinal axis; and wherein the handpiece head is pivotally coupled to the handpiece body to permit adjustable movement of the handpiece head at variable angles with respect to the handpiece body.

2. The medical laser delivery system of claim wherein the handpiece is adapted to be secured to a collar rotatably connected to the delivery arm such that the handpiece rotates with the collar with respect to the delivery arm.

3. The medical laser delivery system of claim 1 wherein the handpiece head is coupled to the handpiece body by a ball and socket joint.

4. The medical laser delivery system of claim 1, wherein the handpiece transmission means includes a removable fiber extension positioned within the handpiece, the fiber extension transmitting the laser energy received from the delivery arm to the distal delivery system when the laser source is actuated.

5. The medical laser delivery system of claim 4, further including a collet chuck positioned within the handpiece, wherein the fiber extension removably mates with the collet chuck to hold the fiber extension in position to receive the laser energy from the delivery arm.

6. The medical laser delivery system of claim 4 wherein the distal delivery system includes a tip through which the laser energy is delivered to the surgical site, the fiber extension transmitting the laser energy received from the delivery arm to the tip.

7. A medical laser delivery system usable in conjunction with a laser energy source and a delivered arm coupled to the laser energy source to transmit laser energy, comprising:
 a handpiece adapted for rotatable coupling to the delivery arm, the handpiece including transmission means for transmitting the laser energy received from the delivery arm, the handpiece being rotatable about its longitudinal axis;
 means for preventing the handpiece from decoupling from the delivery arm when rotating the handpiece during use; and
 a distal delivery system coupled to the handpiece, the distal delivery system delivering the laser energy received from the handpiece to a surgical site when the laser energy source is actuated;
 wherein the handpiece includes a handpiece body for rotatable coupling to the delivery arm and a handpiece head having one end coupled to the handpiece body and another end coupled to the distal delivery system, the handpiece head being pivotally coupled to the handpiece body to permit adjustable movement of the handpiece head to variable angles with respect to the handpiece body, the fiber extension being flexible and extending interior of the handpiece body and the handpiece head.

8. The medical laser delivery system of claim 7 wherein the handpiece head is rotatably coupled to the handpiece body, the handpiece being rotatable about its longitudinal axis.

9. The medical laser delivery system of claim 8 wherein the handpiece head is coupled to the handpiece body by a ball and socket joint.

10. The medical laser delivery system of claim 7 wherein the distal delivery system includes an interchangeable tip through which the laser energy is delivered to the surgical site.

11. The medical laser delivery system of claim 10 wherein the tip is curved.

12. The medical laser delivery system of claim 7 wherein the distal delivery system includes distal transmission means, a nozzle and a tip, the nozzle being coupled to the handpiece and to the tip, the distal transmission means being positioned within the nozzle and tip for transmitting the laser energy received from the handpiece to the surgical site.

13. The medical laser delivery system of claim 12 wherein the nozzle includes a proximal end portion coupled to the handpiece and a distal end portion coupled to the tip, the distal portion being out of axial alignment with the proximal end portion.

14. The medical laser delivery system of claim 13 wherein the nozzle includes a turning mirror positioned interiorly of the nozzle to reflect the laser energy from the proximal end portion to the distal end portion.

15. The medical laser delivery system of claim 7 wherein the handpiece transmission means includes a removable fiber extension positioned within the handpiece, the fiber extension transmitting the laser energy received from the delivery arm to the distal delivery system when the laser source is actuated.

16. The medical laser delivery system of claim 15, further including a collet chuck positioned within the handpiece, wherein the fiber extension removably mates with the collet chuck to hold the fiber extension in position to receive the laser energy from the delivery arm.

17. The medical laser delivery system of claim 15 wherein the distal delivery system includes a tip through which the laser energy is delivered to the surgical site, the fiber extension transmitting the laser energy received from the delivery arm to the tip.

18. A medical laser delivery system usable in conjunction with a laser energy source and a delivery arm coupled to the laser energy source to transmit laser energy, comprising:
 a handpiece body adapted for coupling to the delivery arm to transmit the laser energy received from the delivery arm;
 a handpiece head rotationally and pivotally coupled to the handpiece body to permit adjustable movement of the handpiece head to variable angles with respect to the body and to permit the handpiece head to rotate about its longitudinal axis with respect to the handpiece body;
 handpiece transmission means located within the handpiece body and the handpiece head for transmitting laser energy received from the delivery arm; and
 a distal delivery system coupled to the handpiece head, the distal delivery system delivering the laser energy received from the handpiece head to a surgical site when the laser energy source is actuated.

19. The medical laser delivery system of claim 18 wherein the handpiece body is adapted for rotatable coupling to the delivery arm such that the handpiece body can rotate about its longitudinal axis, the medical laser delivery system further including a retainer preventing the handpiece body from decoupling from the delivery arm when the handpiece body is rotated during use.

20. The medical laser delivery system of claim 19 wherein the handpiece is adapted to be secured to a collar rotatably connected to the delivery arm such that the handpiece rotates with the collar with respect to the delivery arm.

21. The medical laser delivery system of claim 19 wherein the distal delivery system includes a nozzle and an interchangeable tip releaseably coupled to the nozzle, the nozzle and tip being adapted to transmit the laser energy to the surgical site.

22. The medical laser delivery system of claim 18 wherein the handpiece head is coupled to the body by a ball and socket joint.

23. The medical laser delivery system of claim 18, wherein the handpiece transmission means includes a removable fiber extension positioned within the handpiece body and the handpiece head, the fiber extension being removable from the handpiece body and the delivery arm, the fiber extension transmitting the laser energy received from the delivery arm to the distal delivery system when the laser source is actuated.

24. The medical laser delivery system of claim 23, further including a collet chuck positioned within the handpiece body, wherein the fiber extension is removably coupled to the collet chuck.

25. The medical laser delivery system of claim 18 wherein the distal delivery system includes a nozzle and a tip, the nozzle being coupled to the handpiece head and to the tip, the nozzle and tip being adapted to transmit the laser energy received from the handpiece head to the surgical site.

26. The medical laser delivery system of claim 25 wherein the nozzle includes a proximal end portion coupled to the handpiece head and a distal end portion coupled to the tip, the distal portion being out of axial alignment with the proximal end portion.

27. The medical laser delivery system of claim 26 wherein the nozzle includes a turning mirror positioned interiorly of the nozzle to reflect the laser energy from the proximal end portion to the distal end portion.

28. A medical laser delivery system usable in conjunction with a laser energy source and a delivery arm coupled to the laser energy source to transmit laser energy, comprising;
- a handpiece body adapted for rotatable coupling to the delivery arm to transmit the laser energy received from the delivery arm, the handpiece body being rotatable about its longitudinal axis;
- a handpiece head rotatably coupled to the handpiece body to transmit the laser energy received from the handpiece body, the handpiece head being rotatable about its longitudinal axis;
- handpiece transmission means located within the handpiece body and the handpiece head for transmitting laser energy received from the delivery arm;
- means for preventing the handpiece from decoupling from the delivery arm when rotating the handpiece during use; and
- a distal delivery system coupled to the handpiece head, the distal delivery system delivering the laser energy received from the handpiece head surgical site when the laser energy source is actuated;
- wherein the handpiece head is pivotally coupled to the body to permit adjustable movement of the handpiece head variable angles with respect to the handpiece body.

29. The medical laser delivery system of claim 28 wherein the handpiece body is adapted to be secured to a collar rotatably connected to the delivery arm such that the handpiece body rotates with the collar with respect to the delivery arm.

30. The medical laser delivery system of claim 28 wherein the handpiece head is coupled to the body by a ball and socket joint.

31. The medical laser delivery system of claim 28, wherein the handpiece transmission means includes a removable fiber extension positioned within the handpiece body and the handpiece head, the fiber extension transmitting the laser energy received from the delivery arm to the distal delivery system when the laser source is actuated.

32. The medical laser delivery system of claim 31, further including a collet chuck positioned within the handpiece, wherein the fiber extension is removably coupled to the collet chuck to hold the fiber extension in position to receive the laser energy from the delivery arm.

33. The medical laser delivery system of claim 28 wherein the distal delivery system includes a nozzle and an interchangeable tip releaseably coupled to the nozzle, the nozzle and tip being adapted to transmit the laser energy to the surgical site.

34. The medical laser delivery system of claim 33 wherein the tip is hollow.

35. The medical laser delivery system of claim 28 wherein the distal delivery system includes a nozzle and a tip, the nozzle being coupled between the handpiece head and the tip, the nozzle transmitting the laser energy received from the handpiece head to the tip.

36. The medical laser delivery system of claim 35 wherein the nozzle includes a proximal end portion coupled to the handpiece head and a distal end portion coupled to the tip, the distal end portion being out of alignment with the proximal end portion.

37. The medical laser delivery system of claim 36 wherein the nozzle includes a turning mirror positioned interiorly of the nozzle to reflect the laser energy from the proximal end portion to the distal end portion.

38. A medical laser delivery system for transmitting laser energy from a laser energy source to a surgical site of a patient comprising:
- a delivery arm adapted for coupling to the laser energy source to transmit laser energy received from the laser energy source;
- a handpiece adapted for rotatable coupling to the delivery arm, the handpiece including transmission means for transmitting the laser energy received from the delivery arm, the handpiece being rotatable about its longitudinal axis:
- means for preventing the handpiece from decoupling from the delivery arm when rotating the handpiece during use; and
- a distal delivery system coupled to the handpiece, the distal delivery system delivering the laser energy received from the handpiece to a surgical site when the laser energy source is actuated:
- wherein the handpiece includes a handpiece body adapted for rotatable coupling to the delivery arm and a handpiece head having one end coupled to the handpiece body and another end coupled to the distal delivery system;
- wherein the handpiece head is rotatably coupled to the handpiece body the handpiece head being rotatable about its longitudinal axis; and
- wherein the handpiece head is pivotally coupled to the handpiece body to permit adjustable movement of the handpiece head at variable angles with respect to the handpiece body.

39. The medical laser delivery system of claim 38 wherein the handpiece head is coupled to the handpiece body by a ball and socket joint.

40. The medical laser delivery system of claim 38, wherein the handpiece transmission means includes a removable fiber extension positioned within the handpiece, the fiber extension transmitting the laser energy received from the delivery arm to the distal delivery system when the laser source is actuated.

41. The medical laser delivery system of claim 40, further including a collet chuck positioned within the handpiece, wherein the fiber extension removably mates with the collet chuck to hold the fiber extension in position to receive the laser energy from the delivery arm.

42. The medical laser delivery system of claim 40 wherein the distal delivery system includes distal transmission means and a tip, the distal transmission means being coupled to receive the laser energy from the fiber extension, the tip being adapted to receive the laser energy from the distal transmission means and deliver it to the surgical site.

* * * * *

UNITED STATES PATENT AND TRADEMARK OFFICE
CERTIFICATE OF CORRECTION

PATENT NO. : 5,346,489
DATED : September 13, 1994
INVENTOR(S) : Michael B. Levy and Steven E. Wojcik It is certified that error appears in the above-identified patent and that said Letters Patent is hereby corrected as shown below:

In column 6, claim 2, line 51, after "claim" and before "wherein", please insert --1--.

In column 7, claim 7, line 9, please delete "delivered" and substitute therefor --delivery--.

In column 9, claim 28, line 34, after "head" and before "surgical", please insert --to a--.

In column 10, claim 38, line 17, after "patient" and before "comprising", please insert --,--.

Signed and Sealed this

Seventeenth Day of January, 1995

Attest:

BRUCE LEHMAN

*Attesting Officer*     *Commissioner of Patents and Trademarks*